(12) United States Patent
Nagraj et al.

(10) Patent No.: US 10,001,415 B2
(45) Date of Patent: Jun. 19, 2018

(54) MULTIFUNCTIONAL SENSOR

(71) Applicant: General Electric Company, Schenectady, NY (US)

(72) Inventors: Nandini Nagraj, Niskayuna, NY (US); Timothy Mark Sivavec, Clifton Park, NY (US); Yongjae Lee, Niskayuna, NY (US); Daniel Paik, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 323 days.

(21) Appl. No.: 14/823,852

(22) Filed: Aug. 11, 2015

(65) Prior Publication Data

US 2017/0043095 A1 Feb. 16, 2017

(51) Int. Cl.
| | |
|---|---|
| *G01K 11/06* | (2006.01) |
| *G01F 22/00* | (2006.01) |
| *G01F 23/26* | (2006.01) |
| *G01K 1/02* | (2006.01) |
| *A61M 5/31* | (2006.01) |
| *G01F 23/284* | (2006.01) |

(52) U.S. Cl.
CPC .............. *G01K 11/06* (2013.01); *G01F 22/00* (2013.01); *G01F 23/26* (2013.01); *G01K 1/024* (2013.01); *A61M 2005/3125* (2013.01); *A61M 2205/0227* (2013.01); *A61M 2205/3368* (2013.01); *G01F 23/284* (2013.01)

(58) Field of Classification Search
CPC .......... C01K 11/06–11/08; G01K 11/06–11/08
See application file for complete search history.

(56) References Cited

U.S. PATENT DOCUMENTS

| | | | |
|---|---|---|---|
| 4,028,944 A | * | 6/1977 | Erb .................. G01K 11/06 116/201 |
| 6,294,997 B1 | | 9/2001 | Paratore et al. |
| 6,957,623 B2 | | 10/2005 | Guisinger et al. |
| 7,063,041 B2 | | 6/2006 | Odashiro |
| 7,209,042 B2 | | 4/2007 | Martin et al. |
| 7,490,575 B2 | | 2/2009 | Taylor et al. |
| 7,517,146 B2 | | 4/2009 | Smith et al. |
| 7,571,695 B2 | | 8/2009 | Taylor et al. |
| 7,607,829 B2 | | 10/2009 | Sumida et al. |

(Continued)

OTHER PUBLICATIONS

Zhou, Z.; "RFID Usage for Monitoring Drug Dispensing in Hospitals"; School of Computer and Mathematical Science; 2012 (162 pages).

*Primary Examiner* — Clayton E Laballe
*Assistant Examiner* — Leon W Rhodes, Jr.
(74) *Attorney, Agent, or Firm* — Jean K. Testa; Fletcher Yoder, P.C.

(57) ABSTRACT

The subject matter of the present disclosure generally relates to a sensor assembly having a first component configured to melt when a temperature of the sensor assembly reaches a first value below a minimum value of a predetermined temperature range, a second component configured to melt when the temperature of the sensor assembly reaches a second value above a maximum value of the predetermined temperature range, and a third component configured to monitor a volume of fluid disposed in a vessel when the temperature of the sensor assembly is within the predetermined temperature range.

26 Claims, 9 Drawing Sheets

(56) References Cited

U.S. PATENT DOCUMENTS

| | | | |
|---|---|---|---|
| 7,770,534 B2* | 8/2010 | Cooperman | G01K 3/005 |
| | | | 116/206 |
| 7,891,310 B2 | 2/2011 | Taylor et al. | |
| 7,982,612 B2* | 7/2011 | Braun | A61M 5/1684 |
| | | | 340/572.1 |
| 8,122,844 B2 | 2/2012 | Smith et al. | |
| 8,128,872 B2 | 3/2012 | Lentz et al. | |
| 8,267,576 B2 | 9/2012 | Haarer et al. | |
| 8,332,240 B1 | 12/2012 | Garver et al. | |
| 8,542,023 B2 | 9/2013 | Potyrailo et al. | |
| 8,548,623 B2 | 10/2013 | Poutiatine et al. | |
| 8,562,208 B2 | 10/2013 | Yeager et al. | |
| 8,671,871 B2 | 3/2014 | Huffman et al. | |
| 8,957,780 B2* | 2/2015 | Cooperman | G01K 11/06 |
| | | | 340/539.1 |
| 9,581,501 B2* | 2/2017 | Kozono | B32B 7/12 |
| 2007/0056871 A1* | 3/2007 | Griffiths | A61J 1/14 |
| | | | 206/459.1 |
| 2008/0243088 A1 | 10/2008 | Evans | |
| 2009/0123334 A1* | 5/2009 | Cavallini | G01K 11/06 |
| | | | 422/400 |
| 2010/0156606 A1* | 6/2010 | Gold | H04Q 9/00 |
| | | | 340/10.4 |
| 2012/0027045 A1* | 2/2012 | McLellan | G01K 3/04 |
| | | | 374/160 |
| 2012/0245447 A1 | 9/2012 | Karan et al. | |
| 2014/0108027 A1 | 4/2014 | Greyshock et al. | |
| 2014/0200426 A1 | 7/2014 | Taub et al. | |

\* cited by examiner

MULTIFUNCTIONAL SENSOR

BACKGROUND OF THE INVENTION

The subject matter disclosed herein relates to multifunctional sensors, and specifically, to sensors that may be utilized for monitoring fluid dispension and temperature thresholds.

As medication technology continues to improve, medications and vaccines are continuously becoming more complex. In certain instances, medications and vaccines may be stored and dispensed above or below ambient temperature (e.g., room temperature). Further, some medications may be more effective when transported, stored, and dispensed within specific temperature ranges. Therefore, when a medication or vaccine reaches a temperature outside of such range, the medication or vaccine may become less effective or even unfit to perform a desired result (e.g., treating a patient). In other cases, effectiveness of a given medication or vaccine may be at least partially dependent on an amount (e.g., a volume) provided to the patient, or a rate of dispension (e.g., volume over time) to the patient. For example, dispensing too much or too little of a medication or vaccine may be undesirable. Therefore, it is now recognized that a sensor that may monitor when a temperature exceeds threshold values as well as determines how much of the volume has been dispensed may be desired.

BRIEF DESCRIPTION OF THE INVENTION

In one embodiment, a sensor assembly includes a first component configured to melt when a temperature of the sensor assembly reaches a first value below a minimum value of a predetermined temperature range, a second component configured to melt when the temperature of the sensor assembly reaches a second value above a maximum value of the predetermined temperature range, and a third component configured to monitor a volume of fluid disposed in a vessel when the temperature of the sensor assembly is within the predetermined temperature range.

In another embodiment, a method includes monitoring a volume of fluid in a vessel, determining whether a temperature of the fluid in the vessel is outside of a predetermined temperature range, producing an indicator warning against dispension of the fluid from the vessel when the temperature is outside of the predetermined temperature range, and blocking the monitoring of the volume of the fluid in the vessel when the temperature reaches a value outside of the predetermined temperature range.

In another embodiment, a sensor assembly includes a syringe configured to dispense a liquid medication. The sensor assembly includes a first component disposed on the syringe, wherein the first component has a first chemical compound configured to melt when a temperature of the liquid medication reaches a first value below a minimum value of a predetermined temperature range, a second component disposed on the syringe, wherein the second component has a second chemical compound configured to melt when the temperature of the liquid medication reaches a second value above a maximum value of the predetermined temperature range. The sensor assembly further includes a filter disposed between the first component and the second component and a third component disposed on the syringe, wherein the third component has a sensor tag, the third component is configured to monitor a volume of the liquid medication in the vessel when the temperature of the fluid is within the predetermined temperature range, and a signal of the sensor decreases when one or both of the first component and the second component melts. The sensor assembly also includes a protection package comprising a barrier configured to block moisture from contacting the sensor tag.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION OF THE INVENTION

Figure 1:
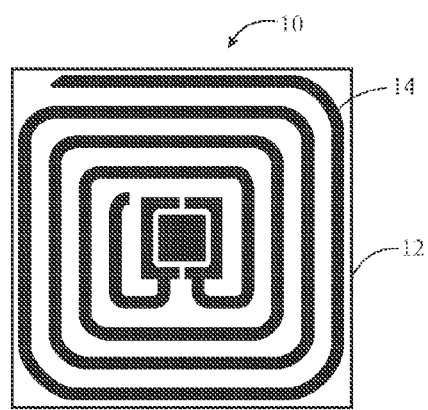
FIG. 1 shows an RF sensor tag that may be used to monitor when a temperature of a fluid reaches a value outside of a predetermined range as well as a volume of the fluid dispensed from a vessel, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A volume of fluid (e.g., medication, vaccine, saline) dispensed, or a rate of dispension, from a vessel (e.g., tube, vial, or syringe) may be difficult to monitor with precision. In certain cases, the volume or dispension rate administered to a patient may at least partially affect an efficiency of the medication in terms of providing aid to the patient. Determining volume using lines drawn on a vessel (e.g., a syringe) may be unreliable and inaccurate. Further, it may be difficult for a person to accurately detect a level of fluid in the vessel (e.g., a syringe) due to surface tension of the liquid (e.g., some liquid may adhere to walls of the vessel creating uncertainty as to the precise volume). Additionally, in certain instances, a vessel (e.g., tube, vial, or syringe) itself may include features (e.g., walls, protrusions) that block a person from viewing a level of the fluid remaining in the vessel. Therefore, it is now recognized that a sensor that may determine an amount of fluid within the vessel, or a rate of fluid dispension from the vessel (e.g., tube, vial, syringe), is desirable.

In certain instances, medications (e.g., liquid medicines, vaccines, and/or salines) may be more effective when the medication is within a specific temperature range (e.g., 0° Celsius to 42° Celsius ("C")). Accordingly, it may be desirable to monitor a temperature profile of a medication (e.g., a liquid medicine, a vaccine, and/or a saline) within a vessel (e.g., syringe) to ensure an effectiveness of the medication (e.g., liquid medicine, vaccine, and/or saline). In certain instances, medication (e.g., liquid medicine, vaccine, and/or saline) that has reached a temperature outside of the specific temperature range may be permanently less effective for providing care to the patient. In some cases, a person administering medication (e.g., a nurse, a doctor, or a patient) may store the medication (e.g., liquid medicine, vaccine, and/or saline) in a refrigerator or another temperature control unit so that the medication remains within the specific temperature range of effectiveness. However, the person administering the medication has no control over shipment of the medication, or the temperature of the medication prior to reaching its final destination (e.g., a hospital or a home).

In certain embodiments of the present disclosure, a vessel (e.g., a vial, a tube, or a syringe) containing medication (e.g., liquid medicine, vaccine, and/or saline) may caution against dispension when the medication has reached a temperature beyond the specific temperature range. For example, when the medication, or the container of the medication, reaches a temperature outside a predetermined temperature range (e.g., either above a maximum value or below a minimum value of the predetermined temperature range), the vessel (e.g., syringe), or a housing containing the vessel, may provide an indicative warning including, but not limited to, notifications on mobile devices, visual cues, or the like. The indicative warning may caution against dispension of the medication (e.g., liquid medicine, vaccine, and/or saline). Additionally, the volume monitoring, or dispension rate monitoring, function may be disabled if a temperature reaches a value outside the predetermined temperature range, thereby providing a further indication that dispension may not be effective.

It is now recognized that a sensor that can detect if a medication has reached a temperature outside of a predetermined temperature range of effectiveness, as well as detect a volume of fluid present within a vessel (e.g., syringe), is desirable to provide accurate and effective medication dispension.

Referring now to the figures, FIG. 1 shows an embodiment of a sensor tag 10 that may be utilized in accordance with aspects of the present disclosure. FIG. 1 illustrates the sensor tag 10 having a radio frequency-based (RF) platform as a transducer. Additionally, the sensor tag 10 has a sensing material 12 disposed upon either an entire antenna coil 14 or smaller portions of the antenna coil 14, thereby enabling an impedance response of the sensor tag 10 when various conditions occur (e.g., temperature changes, volume changes). In another embodiment, the transducer may be an inductor-capacitor-resistor (LCR) resonator, a thickness shear mode resonator, an interdigital electrode structure, or a general electrode structure. It should be recognized that the sensor tag 10 may have any suitable transducer, in accordance with aspects the present disclosure. In one embodiment, the transducer may function over a frequency range from sub kilohertz (kHz) to several Gigahertz (GHz).

Figure 2:
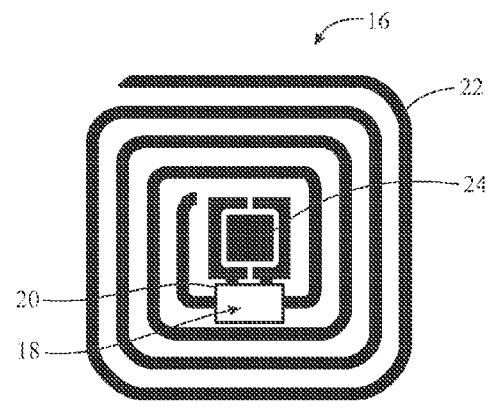
FIG. 2 shows another embodiment of an RF sensor tag with a complementary sensing region, in accordance with aspects of the present disclosure.

FIG. 2 illustrates another embodiment comprising a sensor tag 16 with an RF-based platform as a transducer. In contrast to FIG. 1, a sensing material 18 is disposed upon a complementary sensing region 20 of the sensor tag 16, rather than disposed on the entire antenna 22. The complementary sensing region 20 may be defined as the region of the sensor tag 16 where the antenna 22 and an integrated circuit ("IC") memory chip 24 come in contact, or overlap. The sensing material 18 disposed on the complementary sensing region 20 also alters the impedance response of the sensor tag 16 when various conditions occur (e.g., temperature changes). In another embodiment, the transducer may be an inductor-capacitor-resistor (LCR) resonator, a thickness shear mode resonator, an interdigital electrode structure, or a general electrode structure. The relatively small size of the complementary sensing region 20 when compared to the whole antenna 22 may lead to reduced costs of the applied sensing material. Also, fabrication of a microscale size gap between electrodes in the complementary sensing region 20 may be simplified. Non-limiting examples of complementary sensors are interdigitated sensors, resistive sensors, and capacitive sensors. Complementary sensors are described in U.S. Pat. No. 7,911,345 entitled "Methods and Systems for Calibration of RFID Sensors," which is incorporated herein by reference.

Figure 3:
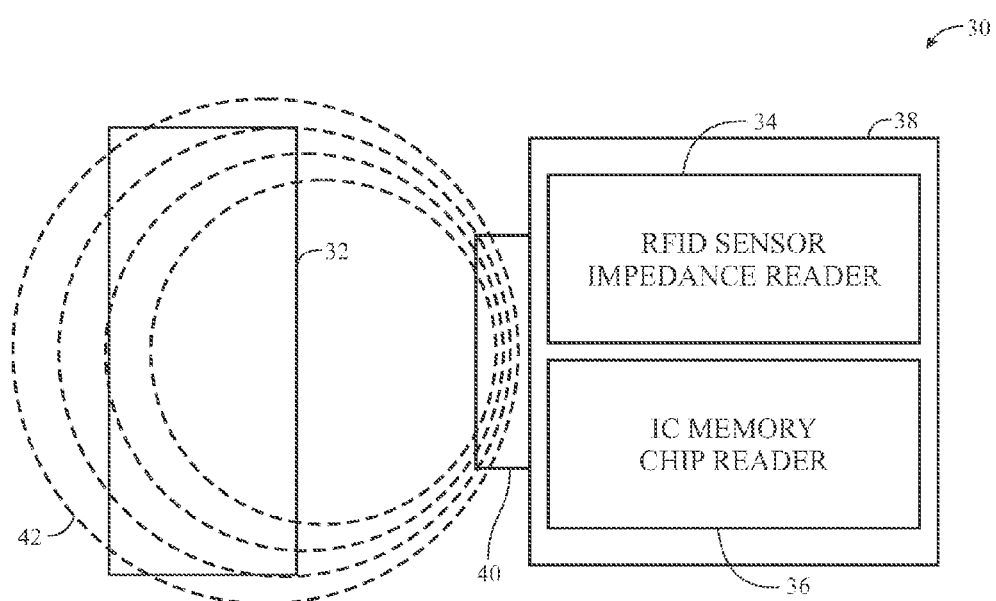
FIG. 3 is a schematic representation of a sensor tag and a sensor reader, in accordance with aspects of the present disclosure.

FIG. 3 shows one embodiment of a sensor assembly 30 that may be used in accordance with aspects of the present disclosure. In certain embodiments, a sensor tag 32 with a passive, or battery-free, RF-based platform transducer includes an RF-based sensor impedance reader 34 with an IC memory chip reader 36 housed within an RF reader 38. A pick-up coil 40 (e.g., a receiver or a receptor) may emit an electromagnetic field 42 in order to read a signal emitted from the sensor tag 32. This information is communicated (e.g., via a wired connection or wireless connection) to a device (e.g., a hub or a cloud-based server) or onto the IC memory chip reader 36. The impedance Z(f) of the sensor tag 32 is measured via inductive coupling between the pick-up coil 40 and the sensor tag 32. In certain embodiments, as fluid in a vessel decreases (e.g., is dispensed from the vessel), the impedance and/or frequency exhibited by the sensor tag 32 may change, thus enabling the sensor assembly 30 to accurately detect a volume of fluid in the vessel.

Figure 4:
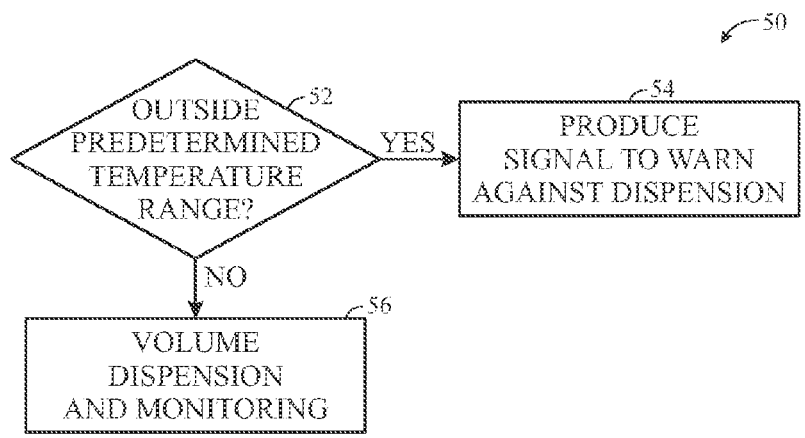
FIG. 4 is a flow chart illustrating a process that a sensor assembly may perform to monitor when a temperature of a fluid reaches a value outside of a predetermined range as well as fluid dispension, in accordance with aspects of the present disclosure.

FIG. 4 is an illustration of a flow chart 50 for a process that a sensor assembly of the present disclosure may perform. As used herein, the sensor assembly may include one or more sensor tags and/or sensing components disposed over a vessel (e.g., a tube, a vial, or a syringe) that contains a fluid (e.g., liquid medicine, vaccine, and/or saline), as well as other components that may provide indicative feedback to a device (e.g., a hub or a cloud-based server) or to a person using and/or monitoring the sensor assembly. In certain embodiments, the sensor assembly may be configured to perform a variety of functions. For example, at block 52, the sensor assembly may be configured to detect if a temperature of the fluid (e.g., liquid medicine, vaccine, and/or saline) within the vessel has reached a value outside of a predetermined temperature range (e.g., between 0° Celsius and 42° Celsius).

Accordingly, at block 54, if the temperature of the fluid (e.g., liquid medicine, vaccine, saline) has reached a value outside of the predetermined temperature range, the sensor assembly may be configured to produce an indicator warning against dispension of the fluid (e.g., liquid medicine, vaccine, saline). For example, the sensor assembly may include a first component (e.g., a first chemical compound such as poloxamer, poly(N-isopropylacrylamide) (PNIPAM), or polyaniline (PANI)) configured to generate a first indicator (e.g., an irreversible change in a signal of the sensor reader 34) when the temperature of the fluid is below a lower limit (e.g., a minimum value) of the predetermined temperature range. In certain embodiments, the first component may include a first chemical compound that has a conducting material such as a highly conductive block copolymer. In other embodiments, the first chemical compound may include a salt, poloxamer, PANI, PANI emeraldine salt doped with organic sulfonic acids, PANI emeraldine salt on carbon black support, polypyrrole doped with an organic sulfonic acid, polypyrrole doped with an organic sulfonic acid on a carbon black support, copper powder, copper granules, copper foil, mesoporous carbon containing graphitic carbon a highly conductive, or any combination thereof.

Similarly, the sensor assembly may include a second component that includes a second chemical compound. In some embodiments, the second chemical compound may include a mixture of a wax (e.g., docosane, heneicosane, lauric acid) and a conductive or semi-conductive material (e.g., PANI, doped PANI derivatives, polypyyroles, graphitized carbon copper, metal particles, metal granules, conductive carbon materials, conductive polymers, or any combination thereof). The second component may be configured to generate a second indicator (e.g., an irreversible change in a signal of the sensor reader 34) when the temperature of the fluid is above an upper limit (e.g., a maximum value) of the predetermined temperature range. In certain embodiments, the sensor assembly may undergo a permanent change when the temperature of the fluid (e.g., liquid medicine, vaccine, saline) reaches a value outside of the predetermined temperature range.

Further, the sensor assembly may include a third component (e.g., an RF sensor tag) that is configured to detect (and record) the two melting events when the temperature of the sensor assembly reaches a value outside of the predetermined temperature range. The third component may also be configured to monitor (e.g., continuously measure) a volume, or a dispension rate, of the fluid (e.g., liquid medicine, vaccine, and/or saline) in the vessel (e.g., a syringe). In certain embodiments, an ability of the third component to perform volume monitoring may be disabled when the first component and/or the second component melt as a result of the temperature of the fluid reaching a value outside the predetermined temperature range. For example, the first and second components may include chemical compounds configured to melt when the temperature of the fluid (e.g., liquid medicine, vaccine, and/or saline) reaches the minimum and/or maximum values of the predetermined temperature range. Accordingly, the melted chemical compound may create a short in the third component (e.g., the sensor tag 32), thereby changing the signal to indicate that the temperature of the fluid has reached a value outside of the predetermined range. This signal change may disable the ability of the sensor assembly to monitor the volume of fluid (e.g., liquid medicine, vaccine, and/or saline) in the vessel (e.g., a syringe), or rate of dispension of fluid from the vessel. Disabling the monitoring ability of the sensor assembly may further caution that the fluid (e.g., liquid medicine, vaccine, and/or saline) has reached a temperature outside of the predetermined temperature range, and thus, is no longer as effective (e.g., suitable for treating a patient) as desired.

At block 56, if the temperature of the fluid (e.g., liquid medicine, vaccine, and/or saline) remains inside of the predetermined temperature range (e.g., does not reach a value outside of 0° Celsius and 42° Celsius) then no indicator warning against dispension of the fluid (e.g., liquid medicine, vaccine, and/or saline) may be triggered. In certain embodiments, the sensor assembly may include indicative warnings that may include notifications on mobile devices, notifications on dispensing devices, and/or other visual cues, for example. In other embodiments, disabling the ability of the sensor assembly to monitor the amount of volume in the vessel may serve as the indicative warning.

When the temperature of the fluid (e.g., liquid medicine, vaccine, and/or saline) is within the predetermined temperature range, the monitoring feature of the sensor assembly may be (e.g., remain) activated. Therefore, as the fluid (e.g., liquid medicine, vaccine, and/or saline) is dispensed from the vessel (e.g., a syringe), the third component (e.g., an RF sensor tag) may monitor and detect how much of the fluid (e.g., liquid medicine, vaccine, and/or saline) remains in the vessel (e.g., syringe). In other embodiments, the third component (e.g., an RF sensor tag) may be configured to monitor a rate of fluid (e.g., liquid medicine, vaccine, and/or saline) dispension from the vessel (e.g., syringe). In any event, real time monitoring of an amount of fluid (e.g., liquid medicine, vaccine, and/or saline) in the vessel (e.g., syringe) may be performed so that a desired amount, or rate, of fluid (e.g., liquid medicine, vaccine, and/or saline) is dispensed. Therefore, in embodiments where the fluid is medication (e.g., liquid medicine, vaccine, and/or saline), an accurate dose of medication may be constantly administered to a patient.

Figure 5:
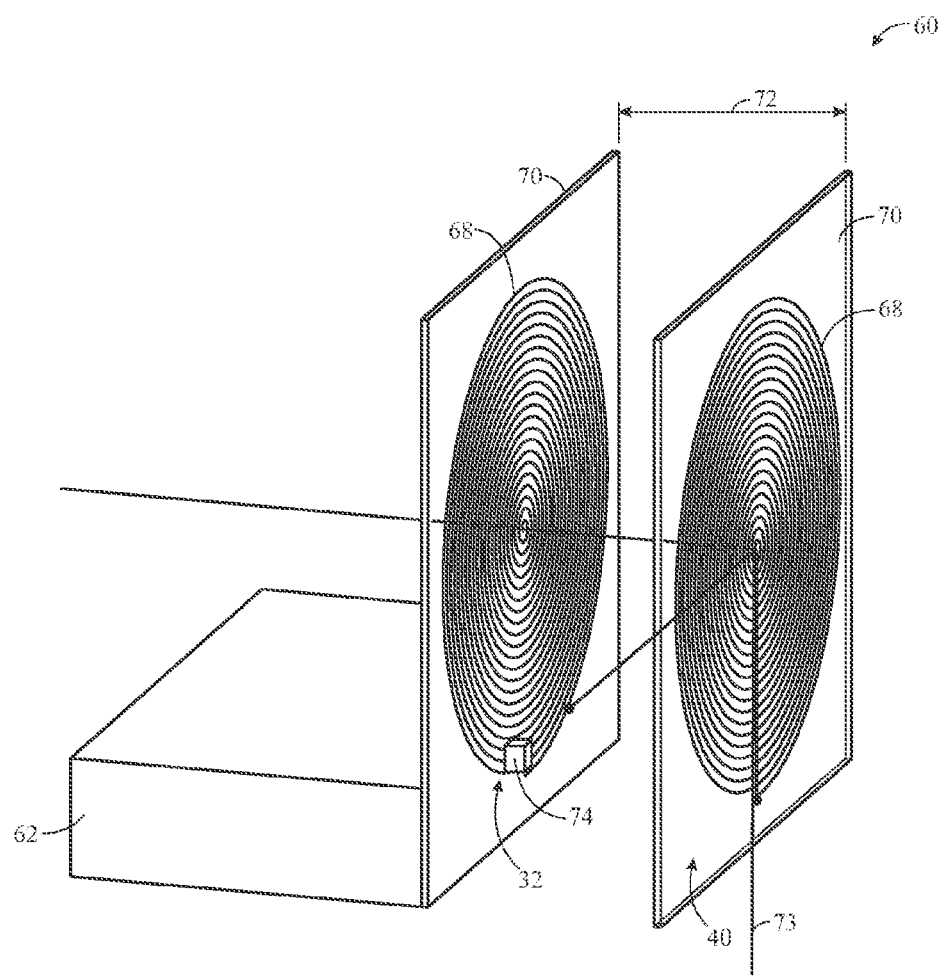
FIG. 5 illustrates an embodiment of a component that may be configured to measure a volume of fluid in a vessel, in accordance with aspects of the present disclosure.

FIG. 5 illustrates an embodiment of the third component 60 that may be configured to measure a volume of fluid 62 (e.g., liquid medicine, vaccine, and/or saline) in the vessel (e.g., syringe). Similar to the sensor assembly 30 of FIG. 3, the third component 60 includes the sensor tag 32 and the pick-up coil 40 (e.g., a receiver or receptor). As shown in the illustrated embodiment, the sensor tag 32 and the pick-up coil 40 may each include a metal portion 68 (e.g., the antenna 22) configured in a spiral shape and disposed on a substrate 70. The metal portion 68 may include between 25 and 100 turns, between 30 and 80 turns, or between 50 and 75 turns, for instance. Additionally, the metal portion 68 may include a width between each turn that is between 5 micrometers and 100 micrometers, between 25 micrometers and 90 micrometers, or between 50 micrometers and 75 micrometers, for instance. Further, the metal portion 68 may include a thickness of between 1 micrometer and 20 micrometers, between 2 micrometers and 15 micrometers, or between 3 micrometers and 10 micrometers, for instance. It should be noted that in other embodiments, the sensor tag 32 and the pick-up coil 40 may include a metal portion (e.g., the antenna 22) having the configuration (e.g., square shape) shown in FIGS. 1 and 2.

In certain embodiments, the sensor tag 32 may be disposed on the vessel (e.g., contacting the vessel), the vessel may be placed in a housing, and the pick-up coil 40 may be disposed on the housing. Accordingly, a gap 72 (e.g., an opening or a space) between the sensor tag 32 and the pick-up coil 40 may be formed. In certain embodiments, the gap 72 is between 1 millimeter and 10 millimeters, between 2 millimeters and 8 millimeters, or between 3 millimeters and 5 millimeters, for instance. Additionally, the gap 72 may be filled with air, or any other suitable substance that may enable inductive coupling (e.g., via a magnetic field) between the sensor tag 32 and the pick-up coil 40. In other embodiments, components configured to detect when a temperature of the fluid 62 in the vessel is outside of the predetermined temperature range may be positioned between the sensor tag 32 and the pick-up coil 40 (e.g., disposed over the sensor tag 32). In still further embodiments, both of the components configured to detect when the temperature is outside of the predetermined temperature range may be in the gap 72.

To monitor the volume of the fluid 62 in the vessel, the pick-up coil 40 may be coupled to a lead 73 that sends feedback indicative of the volume of the fluid 62 to a controller, a reader (e.g., the RF sensor impedance reader 34), or a display that indicates how much volume of the fluid 62 has been dispensed from the vessel, or the rate of fluid dispension from the vessel. In certain embodiments, the pick-up coil 40 may emit an electromagnetic field, for example, that may read a signal emitted from the sensor tag 32. In certain embodiments, the sensor tag 32 may be configured to emit a signal (e.g., an impedance value or frequency value) indicating a volume of the fluid 62 in the vessel. In certain embodiments, a non-metal portion of the sensor tag 32 may enable the sensor tag 32 to undergo changes in resonant frequency as the volume of the fluid 62 varies in the vessel. Accordingly, the signal generated by the sensor tag 32 may correspond to a resonant frequency that changes as the amount of volume of the fluid 62 varies within the vessel (e.g., as the amount of fluid 62 decreases, the resonant frequency of the sensor tag 32 may increase, or vice versa). The electromagnetic field generated by the pick-up coil 40 may then detect such a signal from the sensor tag 32, thereby enabling a person to monitor how much of the fluid 62 has been dispensed from the vessel, or a rate of fluid dispension from the vessel.

Figure 6:
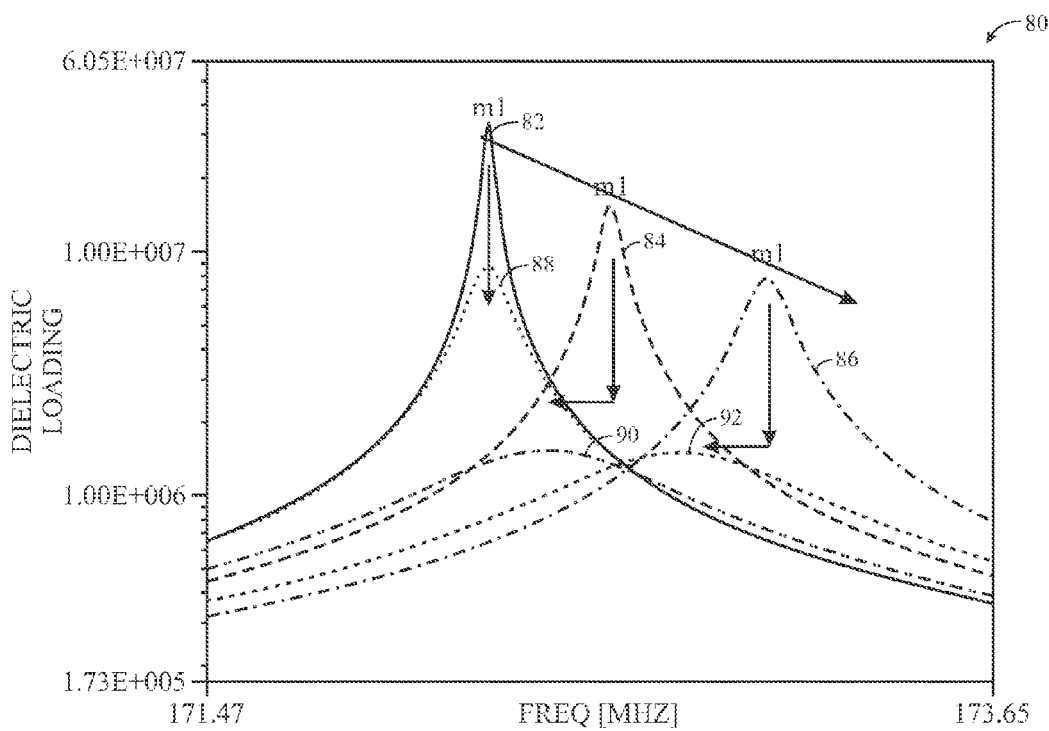
FIG. 6 is a graphical representation of a predicted dielectric loading as a function of resonant frequency of a sensor assembly as a volume of fluid decreases in the vessel, in accordance with aspects of the present disclosure.

FIG. 6 is a graphical representation 80 of dielectric loading as a function of resonant frequency of the sensor assembly as a volume of the fluid 62 (e.g., liquid medicine, vaccine, and/or saline) decreases in the vessel (e.g., syringe). As shown in the graph 80, a first curve 82 shows the dielectric loading and resonant frequency of the sensor assembly when the volume of the fluid 62 fills approximately 90% of the vessel (e.g., syringe). Similarly, a second curve 84 shows the dielectric loading and resonant frequency of the sensor assembly when the vessel is approximately 15% full, and a third curve 86 shows the dielectric loading and resonant frequency of the sensor assembly when the vessel is approximately 5% full.

As illustrated in FIG. 6, the first curve 82, which represents the vessel having the most amount of the fluid 62, is furthest to the left (e.g., the first curve 82 has the lowest value of resonant frequency). Accordingly, the graph 80 illustrates that the resonant frequency of the sensor tag 32 and the volume of the fluid 62 within the vessel (e.g., a syringe) have an inversely proportional relationship. In other words, as the volume of the fluid 62 decreases, resonant frequency increases. Conversely, the amount of fluid 62 dispensed from the vessel (e.g., a syringe) has a proportional relationship to resonant frequency (e.g., resonant frequency increases as more fluid 62 is dispensed). Additionally, the first curve 82 has the highest value representing dielectric loading. Therefore, the graph 80 also illustrates the relationship between the volume of the fluid 62 in the vessel and the associated dielectric loading of the sensor assembly. For example, the more fluid 62 in the vessel, the higher the dielectric loading of the sensor assembly.

Additionally, FIG. 6 compares a response of the sensor assembly when the sensor tag 32 includes the sensing material 74 with various conductivities. For example, the first curve 82 represents the response of the sensor assembly when the fluid 62 fills approximately 90% of the vessel and when the sensing material 72 has a relatively low conductivity (e.g., less than one one-thousandth Siemens per meter). Conversely, a fourth curve 88 represents the response of the sensor assembly when the fluid 62 fills approximately 90% of the vessel, but the sensing material 72 has a relatively high conductivity (e.g., approximately 1 Siemens per meter). As shown in the illustrated embodiment of FIG. 6, the dielectric loading decreases fairly significantly as the conductivity of the sensing material 74 increases.

Additionally, the graph 80 shows that frequency may also decrease as the conductivity of the sensing material 74 increases. For example, the second curve 84 representing a vessel filled approximately 15% with the fluid 62 and having a sensing material with a relatively low conductivity (e.g., less than one one-thousandth Siemens per meter) has a higher frequency than a fifth curve 90 that also represents a vessel filled approximately 15% with the fluid, but having a sensing material with a relatively high conductivity (e.g., approximately one Siemens per meter). Similarly, the third curve 86 representing a vessel filled approximately 5% with the fluid 62 and having a sensing material with a relatively low conductivity (e.g., less than one one-thousandth Siemens per meter) has a higher frequency than a sixth curve 92 that also represents a vessel filled approximately 5% with the fluid, but having a sensing material with a relatively high conductivity (e.g., approximately one Siemens per meter). It may be desirable to utilize a sensing material that includes a suitable conductivity enabling the sensor tag 32 to accurately detect an amount of volume of the fluid 62 in the vessel.

It should be noted that the response of the sensor tag 32 to an amount of the fluid 62 in the vessel may also depend on the size of the sensing material. The sensing materials used to collect the data for FIG. 6 had dimensions of 0.5 millimeters by 0.5 millimeters by 0.2 millimeters (e.g., length by width by height). However, it should be recognized that the sensing material 74 may be any suitable size that enables the sensor assembly to undergo a change in frequency as the volume of the fluid 62 varies.

Figure 7:
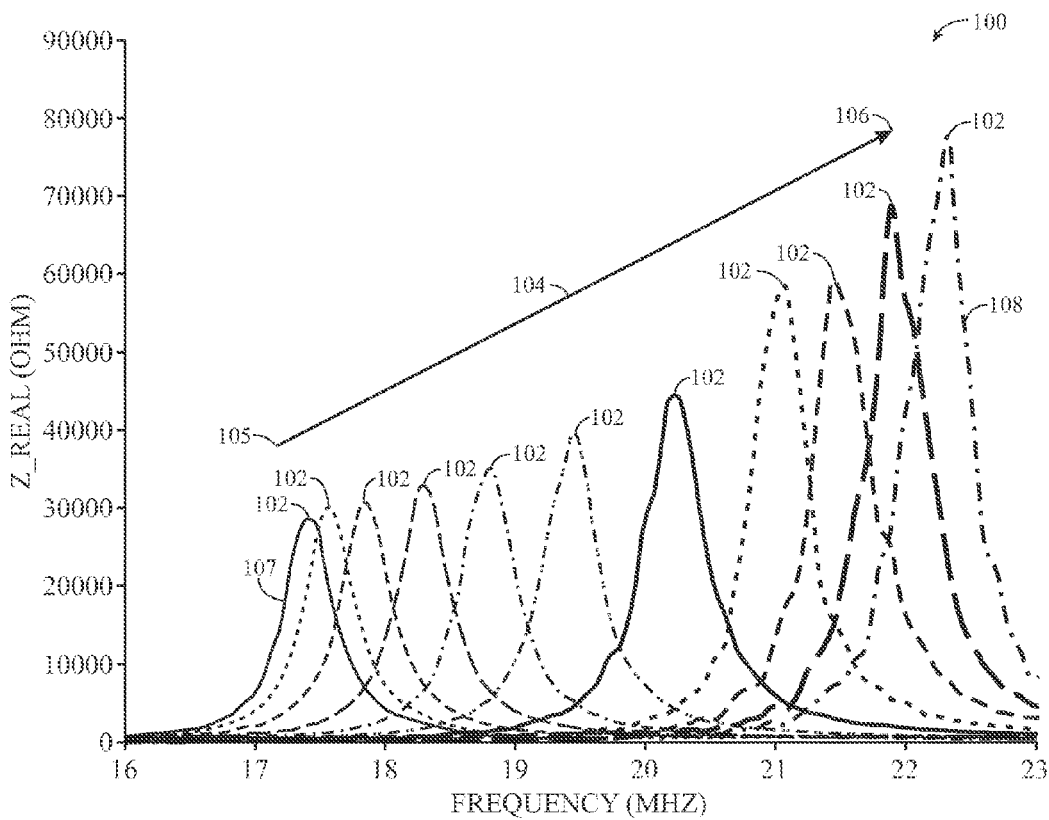
FIG. 7 illustrates a graphical representation showing spectral parameters, which include frequency and amplitude, of a sensor assembly increasing as fluid is dispensed from the vessel, in accordance with aspects of the present disclosure.

FIG. 7 illustrates a graphical representation 100 showing a spectrum change of the sensor tag 32 response. Specifically, FIG. 7 shows how frequency increases as volume of the fluid 62 dispensed increases. Graph 100 shows a plurality of curves 102 plotting frequency as a function of impedance. Each curve of the plurality of curves 102 represents a different amount of volume of the fluid 62 in the vessel. For example, line 104 represents volume of the fluid 62 in the vessel. The line 104 includes a first end 105 representing the scenario where the vessel includes the largest volume of the fluid 62. Conversely, the line 104 has a second end 106 that represents when the vessel has the least amount of volume of the fluid 62. As shown in the illustrated embodiment of FIG. 7, a curve 107 on the first end 105 of the line 104 has the lowest frequency and impedance values, meaning that when the vessel has the most volume of the fluid 62 (e.g., the least amount of fluid 62 dispensed from the vessel), the sensor tag 32 emits a low frequency and low impedance signal. Conversely, a curve 108 on the second end 106 of the line 104 has the highest frequency and highest impedance values, meaning that when the vessel has the least amount of the fluid 62 (e.g., the most amount of the fluid 62 dispensed from the vessel), the sensor tag 32 emits a high frequency and high impedance signal. Graph 100 also shows that frequency increases as the fluid 62 in the vessel decreases (e.g., more of the fluid 62 is dispensed). Additionally, the graph 100 shows that impedance increases as the amount of the fluid 62 in the vessel decreases. In other words, the volume of the fluid 62 in the vessel is inversely proportionate to impedance.

Figure 8:
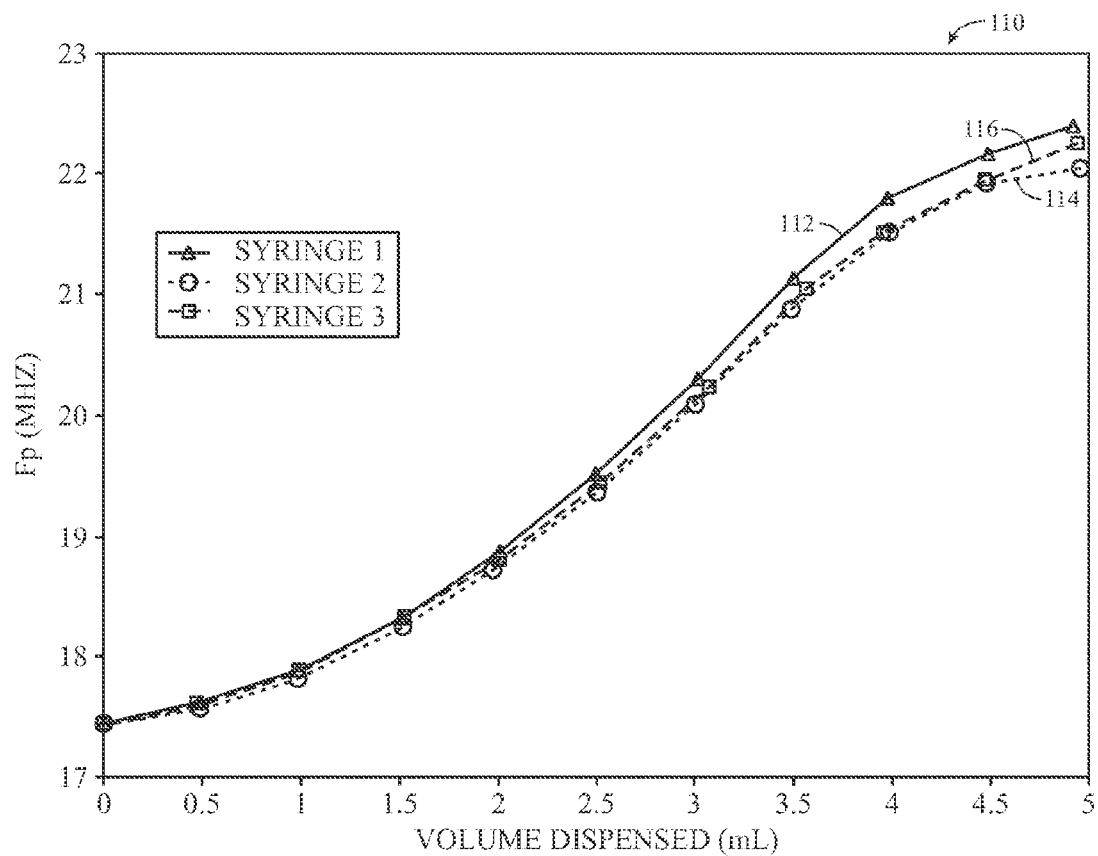
FIG. 8 illustrates a graphical representation of peak frequency change of a sensor assembly as a function of volume of fluid dispensed from the vessel, in accordance with aspects of the present disclosure.

Similarly FIG. 8 illustrates a graphical representation 110 of a change in resonant frequency of a sensor assembly as a function of volume of the fluid 62 dispensed from the vessel (e.g., syringe). In the illustrated embodiment of FIG. 8, a first curve 112, a second curve 114, and a third curve 116 correspond to the change in resonant frequency of three different sensor assemblies. The graph of FIG. 8 illustrates that as more volume is dispensed from the vessel (e.g., syringe), frequency increases. In certain embodiments, the graph 110 may be utilized to develop a calibration curve that predicts how much of the fluid 62 (e.g., liquid medicine, vaccine, and/or saline) is present in the vessel (e.g., syringe). For instance, experimental data (e.g., data correlating frequency to volume) may enable generation of the calibration curve, which may be utilized to accurately detect the amount of volume of the fluid 62 in the vessel (or dispensed from the vessel) based on a frequency measurement detected by the pick-up coil 40.

Figure 9:
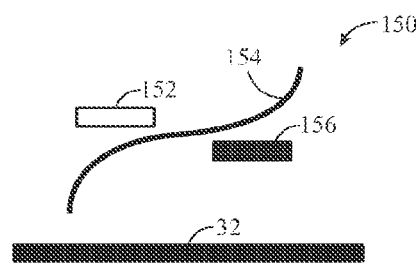
FIG. 9 illustrates an embodiment of a portion of a sensor assembly having a first component disposed on a first side a filter and a second component disposed on a second side of the filter, in accordance with aspects of the present disclosure.

As discussed above, in addition to the ability of the sensor assembly to measure volume, the sensor assembly may also be configured to monitor and/or detect whether a temperature of the fluid 62 in the vessel reaches a value outside of the predetermined temperature range via the first and the second components. FIG. 9 illustrates one embodiment of a portion of a sensor assembly 150 that may be used in accordance with aspects of the present disclosure. For example, a first component 152 may be placed above a filter 154 and a second component 156 may be disposed below the filter 154. The first and second components 152, 156 along with the filter 154 may then be disposed over the sensor tag 32 of the third component 60. In certain embodiments, the first component 152, the filter 154, the second component 156 and the sensor tag 32 may be disposed over the vessel, and the vessel may be disposed in a housing. Further, the pick-up coil 40 may be positioned outside of the housing (e.g., space between the housing and the vessel forms the gap 72). In other embodiments, the pick-up coil 40 may be disposed in the housing with the sensor tag 32.

In certain embodiments, the vessel may be cylindrical in shape and thus, the sensor assembly 150 may be flexible such that it may be wrapped around the vessel and conform to the cylindrical shape. In other embodiments, the vessel may be a rectangular prism, where the sensor assembly 150 may lay flat against a surface of the vessel.

In certain embodiments, the first and second components 152, 156 may be configured to determine when the temperature of the fluid 62 is below a minimum value of a predetermined temperature range and above a maximum value of the predetermined temperature range, respectively. In other embodiments, the first and second components 152, 156 may each be able to determine when the temperature of the fluid 62 is outside of the predetermined temperature range regardless of whether the temperature is below the minimum value or beyond the maximum value.

In certain embodiments, the first component 152 may be configured to detect when the temperature of the fluid 62 is below a minimum value of the predetermined temperature range. For instance, the first component 152 may include a first chemical compound that responds or reacts when exposed to an environment having a temperature below the minimum value (e.g., 0° Celsius) of the predetermined temperature range. In certain embodiments, the first chemical compound may be configured to be in a solid state when the temperature of the sensor assembly 150 is within the predetermined range, but in a liquid state when the temperature of the sensor assembly 150 falls below the minimum value (e.g., 0° Celsius) of the predetermined temperature range. For example, the first chemical compound may include a poloxamer with a conductive material (e.g., a salt, PANI, PANI emeraldine salt doped with organic sulfonic acids, PANI emeraldine salt on carbon black support, polypyrrole doped with an organic sulfonic acid, polypyrrole doped with an organic sulfonic acid on a carbon black support, copper powder, copper granules, copper foil, mesoporous carbon containing graphitic carbon a highly conductive, or any combination thereof). A hydrogel containing the poloxamer material may transition from a solid state to a liquid state upon a decrease in temperature. Therefore, the first chemical compound may be configured to include a concentration of poloxamer material that enables the first chemical compound to undergo the transition from solid to liquid at the minimum value (e.g., 0° Celsius) of the predetermined temperature range. For example, the first chemical compound may include between 10% and 90% poloxamer by weight, between 25% and 75% poloxamer by weight, or between 40% and 60% poloxamer by weight, depending on the desired predetermined temperature range. However, it should be noted that the first component may include any substance configured to transition from a solid state to a liquid state upon a decrease in temperature.

In certain embodiments, the first chemical compound may be in gel form when the temperature of the fluid 62 is within the predetermined temperature range, and melt into a liquid form when the temperature reaches the minimum value (e.g., 0° C.) of the predetermined temperature range. Conversely, the first chemical compound may remain in the solid state when the temperature of the fluid 62 reaches a value above the maximum value of the predetermined temperature range (e.g., 42° Celsius). When the first chemical compound melts into the liquid state, the resulting liquid may contact the sensor tag 32 of the third component 60, thereby affecting an electrical circuit of the sensor tag 32 and causing the sensor tag 32 to incur a decrease in signal (e.g., decreasing an impedance signal of the sensor tag 32). In certain embodiments, the first chemical compound increases the effect of the liquidized first component such that it may disable or deactivate (e.g., permanently deactivate) the ability of the sensor assembly 150 to measure or monitor a volume of the fluid 62 in the vessel, or a dispension rate of the fluid 62 from the vessel.

In certain embodiments, it may be desirable to limit an area of the sensor assembly 150 to which the melted first chemical compound may spread. Additionally, it may be desirable to protect the sensor assembly 150 from the first chemical compound until the first chemical compound has melted at the minimum temperature of the predetermined temperature range. Therefore, the first component 152 may be disposed on top of the filter 154. In certain embodiments, the filter 154 may include an absorbent material. For example, the filter 154 may be a microfiber (MF) filter that has a retention of between 0.5 micrometer particles and 10 micrometer particles, between 1 micrometer particles and 8 micrometer particles, or between 1 micrometer particles and 2 micrometer particles. Additionally, the MF filter may be between 0.05 millimeters and 5 millimeters thick, between 0.1 millimeters and 2 millimeters thick, or between 0.1 millimeters and 1 millimeter thick. In other embodiments, the filter 154 may include any suitable retention and any suitable thickness to contain the liquid within a desired area. As the first chemical compound melts, the area to which the liquid may spread may be limited because the filter 154 absorbs at least a portion of the liquid, containing the liquid in the area covered by the filter 154. In certain embodiments, limiting the area to which the liquid may spread may concentrate the liquid over the sensor tag 32, and further decrease the response of the sensor tag 32. In still further embodiments, the filter 154 may be configured to act as a barrier such that the filter 154 may block (e.g., temporarily block) the liquidized first component from contacting the third component 60 for a predetermined time. Additionally, in certain embodiments, the filter 154 may be configured to prevent the liquidized first component from evaporating and escaping from the sensor assembly 150.

While the present discussion focuses on the first component having a first chemical compound that melts when the temperature reaches the minimum value of the predetermined temperature range, it should be noted that the first component may exhibit another suitable response to create an alert that the temperature of the fluid has reached a value outside the predetermined temperature range.

In certain embodiments, the second component 156 may be configured to detect when the temperature of the fluid 62 is above a maximum value of the predetermined temperature range. For instance, the second component 156 may include a second chemical compound that responds or reacts when exposed to an environment having a temperature above the maximum value of the predetermined range (e.g., 42° Celsius). In certain embodiments, the second chemical compound may be configured to be in a solid state when the temperature of the sensor assembly 150 is within the predetermined range, but in a liquid state when the temperature of the sensor assembly 150 increases beyond the maximum value (e.g., 42° Celsius) of the predetermined temperature range. For example, the second chemical compound may include a mixture of wax (e.g., docosane, heneicosane, lauric acid), conductive materials, and/or semi-conductive materials (e.g., polyaniline (PANI), copper granules). For example, a mixture of wax and PANI solids may transition from a solid state to a liquid state when the temperature of the fluid 62 exceeds the maximum value of the predetermined temperature range (e.g., 42° Celsius), thereby depositing the solid PANI onto the sensor tag 32. However, it should be noted that the second component may include any substance configured to melt from a solid to a liquid upon an increase in temperature at the maximum value of the predetermined temperature range.

In certain embodiments, the second chemical compound may be in solid or gel form when the temperature of the fluid 62 is within the predetermined temperature range, and melt into a liquid form when the temperature exceeds the maximum value of the predetermined temperature range (e.g., 42° C.). Conversely, the second chemical compound may remain in the solid state when the temperature of the fluid 62 falls below the minimum value of the predetermined temperature range (e.g., 0° Celsius). When the second chemical compound melts into liquid state, the resulting embedded conducting materials and/or semi-conducting materials (e.g., PANI or copper granules) may contact the sensor tag 32 of the third component 60, thereby affecting the electrical circuit of the sensor tag 32 and causing the sensor tag 32 to short and incur a decrease in signal. In certain embodiments, the effect of the liquidized second component may disable or deactivate the ability of the sensor assembly 150 to measure or monitor a volume of the fluid 62 in the vessel. In other embodiments, the liquid may generate an indicator or an alert (e.g., notifications on mobile devices or visual cues) to notify that the fluid 62 has reached a temperature outside of the predetermined temperature range. While the present discussion focuses on the second component having a second chemical compound that melts when the temperature exceeds the maximum value of the predetermined temperature range, it should be noted that the second component may exhibit another suitable response to create an alert that the temperature of the fluid has exceeded a value outside the predetermined temperature range.

In certain embodiments, the second component 156 may be disposed beneath the filter 154 such that when the second chemical compound melts into liquid form, the liquid does not travel through the filter 154 before contacting the sensor tag 32. In other embodiments, the filter 154 may be disposed between the second component 156 and the sensor tag 32 such that the liquidized second chemical compound flows through the filter 154 before contacting the sensor tag 32. Accordingly, some of the liquidized second chemical compound may be absorbed by the filter 154, which may enable the liquidized second chemical compound to be concentrated within a smaller area. The smaller area may enable more of the liquidized second chemical compound to contact the sensor tag 32, which may further decrease the response of the sensor tag 32.

As discussed above, the first component 152 and/or the second component 156 may disable a function of the third component 60 (e.g., monitoring volume of the fluid 62 in the vessel) when the temperature of the fluid 62 reaches a value outside of the predetermined temperature range. Moreover, the first and/or second components 152, 156 may alert (e.g., by creating an indicator or by disabling the third component 60) a person who may dispense the fluid 62 from the vessel that the fluid 62 has reached a temperature outside the predetermined temperature range, and thus, avoid dispension of the fluid 62 when desirable.

Figure 10:
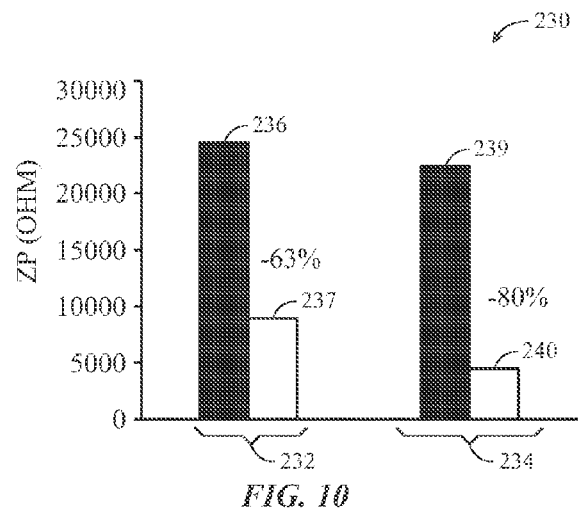
FIG. 10 illustrates a graphical representation of a decrease in a response of the sensor upon exposure to temperatures outside of a predetermined temperature range, in accordance with aspects of the present disclosure.

FIG. 10 is a graphical representation 230 of a response of the sensor tag 32 upon exposure to a liquidized first chemical compound and/or a liquidized second chemical compound. Graph 230 shows two charts 232 and 234 plotting impedance of the sensor tag 32 (e.g., a measure of the response of the sensor tag 32 to temperature changes in the vessel). The chart 232 represents the effect on impedance of the sensor tag 32 when the sensor assembly 150 was exposed to a temperature above the maximum value of the predetermined temperature range. For example, the maximum value of the predetermined temperature range was arbitrarily chosen as 42° Celsius, and the sensor assembly 150 was exposed to an environment having a temperature of 43° Celsius for 15 minutes. The chart 234 represents the effect on impedance of the sensor tag 32 when the sensor assembly 150 was exposed to a temperature below the minimum value of the predetermined temperature range. For example, the minimum value of the predetermined temperature range was arbitrarily chosen as 0° Celsius, and the sensor assembly 150 was exposed to an environment having a temperature of −1.5° Celsius for 45 minutes. It should be noted that while the maximum temperature of the predetermined temperature range was chosen as 42° Celsius and the minimum temperature of the predetermined temperature range was chosen as 0° Celsius for the data presented in FIG. 10, the present disclosure may include a sensor assembly configured to operate within any suitable predetermined temperature range having a minimum and maximum value.

The chart 232 includes two bars 236 and 237. Bar 236 represents the impedance of the sensor tag 32 after being covered (e.g., packaged) with the first component 152, the filter 154, and/or the second component 156 and exposed to an environment having a temperature within the predetermined temperature range. In some embodiments, the response of the sensor tag 32 decreases as a result of disposing the first component 152, the filter 154, and/or the second component 156 over the sensor tag 32. However, despite the decrease in response of the sensor tag 32 to packaging, the sensor assembly 150 may still accurately detect a level of volume of the fluid 62 (e.g., liquid medicine, vaccine, and/or saline) in the vessel.

Bar 237 represents the effect on the sensor tag 32 once exposed to an environment having a temperature above the maximum value of the predetermined temperature range (e.g., exposed to a temperature of 43° Celsius for 15 minutes when the maximum value of predetermined temperature range was 42° Celsius). Upon exposure to the temperature above the maximum value of the predetermined temperature range, the second chemical component (e.g., a mixture of wax and PANI) melted, causing liquid to contact the electrical circuit of the sensor tag 32. Accordingly, the impedance of the sensor tag 32 decreases significantly (e.g., approximately 63% from bar 236), and thus, the sensor tag's 32 response to a change in volume of the fluid 62 in the vessel is substantially limited. In certain embodiments, the impedance change shown between bar 236 and bar 237 may fully inhibit the response of the sensor tag 32, such that the sensor tag 32 may no longer accurately monitor the volume of the fluid 62 (e.g., liquid medicine, vaccine, and/or saline) in the vessel.

Similarly, the chart 234 includes two bars 239 and 240. Bar 239 represents the impedance of the sensor tag 32 after being covered (e.g., packaged) with the first component 152, the filter 154, and/or the second component 156 and exposed to an environment having a temperature within the predetermined temperature range. In certain embodiments, the response of the sensor tag 32 decreases as a result of disposing the first component 152, the filter 154, and/or the second component 156 over the sensor tag 32. However, despite the decrease in response of the sensor tag 32 to the packaging, the sensor assembly 150 may still accurately detect a level of volume of the fluid 62 (e.g., liquid medicine, vaccine, and/or saline) in the vessel.

Bar 240 represents the effect on the sensor tag 32 once exposed to an environment having a temperature below the minimum value of the predetermined temperature range (e.g., exposed to a temperature of −1.5° Celsius for 45 minutes when the minimum value of predetermined temperature range was 0° Celsius). Upon exposure to the temperature below the minimum value of the predetermined temperature range, the first chemical component (e.g., poloxamer) melted, causing liquid to contact the electrical circuit of the sensor tag 32. Accordingly, the impedance of the sensor tag 32 decreases significantly (e.g., approximately 80% from bar 239), and thus, the sensor tag's 32 response to a change in volume of the fluid 62 in the vessel is substantially limited. In certain embodiments, the impedance change shown between bar 239 and bar 240 may fully inhibit the response of the sensor tag 32, such that the sensor tag 32 may no longer accurately monitor the volume of the fluid 62 (e.g., liquid medicine, vaccine, and/or saline) in the vessel. In certain embodiments, this decrease in impedance change may be an indicator that warns or cautions against fluid dispension.

Additionally, FIG. 10 illustrates the effect on the sensor tag 32 when components of the sensor assembly 150 are packaged into a single unit. As discussed above, packaging the sensor assembly 150 (e.g., placing the first component 152, the filter 154, and/or the second component 156 over the third component 60) may inhibit the response of the sensor tag 32. However, packaging may be optimized such that the effect on the response of the sensor tag 32 is minimized. When packaging is optimized, the decrease in the sensor tag's 32 response as a result of packaging is minimized. Therefore, optimizing packaging may enable the sensor tag 32 to exhibit a strong response to a change in volume of the fluid 62 in the vessel when the temperature of the fluid 62 is within the predetermined temperature range.

Figure 11:
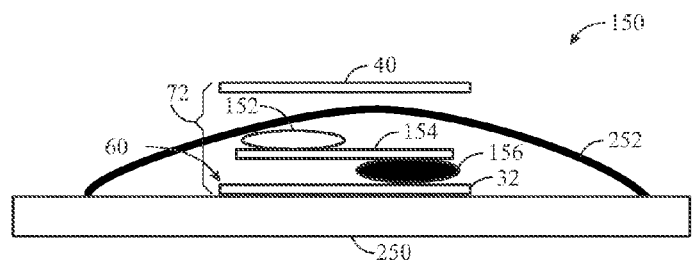
FIG. 11 illustrates an embodiment of a sensor assembly that includes a vessel over which a first component, a second component, a third component, a filter, and a protection package are disposed, in accordance with aspects of the present disclosure.
Figure 12:
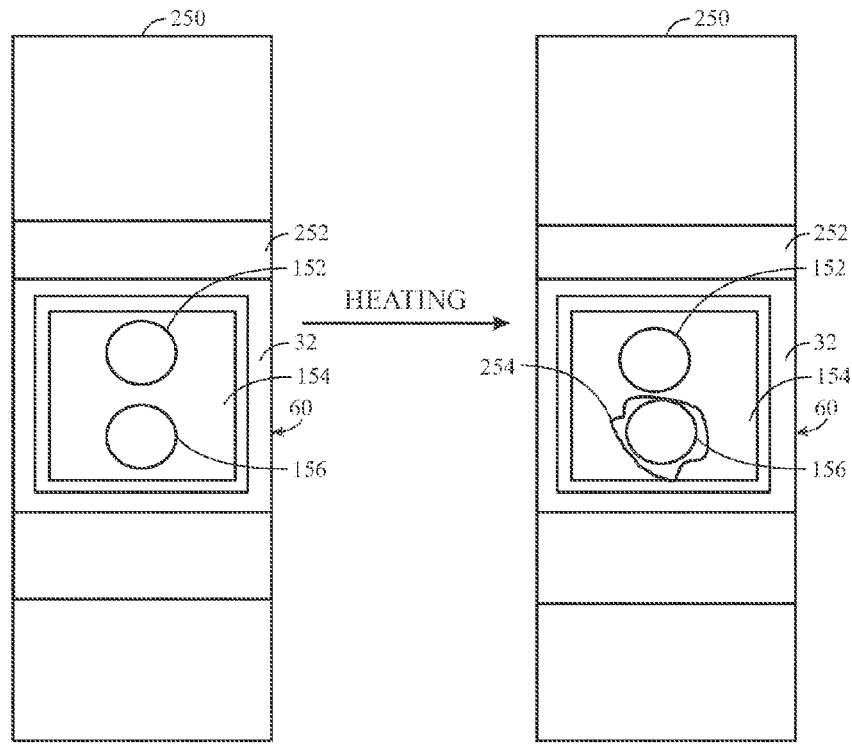
FIG. 12 illustrates a response of a first temperature sensitive component upon exposure to a temperature above a maximum value of a predetermined temperature range, in accordance with aspects of the present disclosure.
Figure 13:
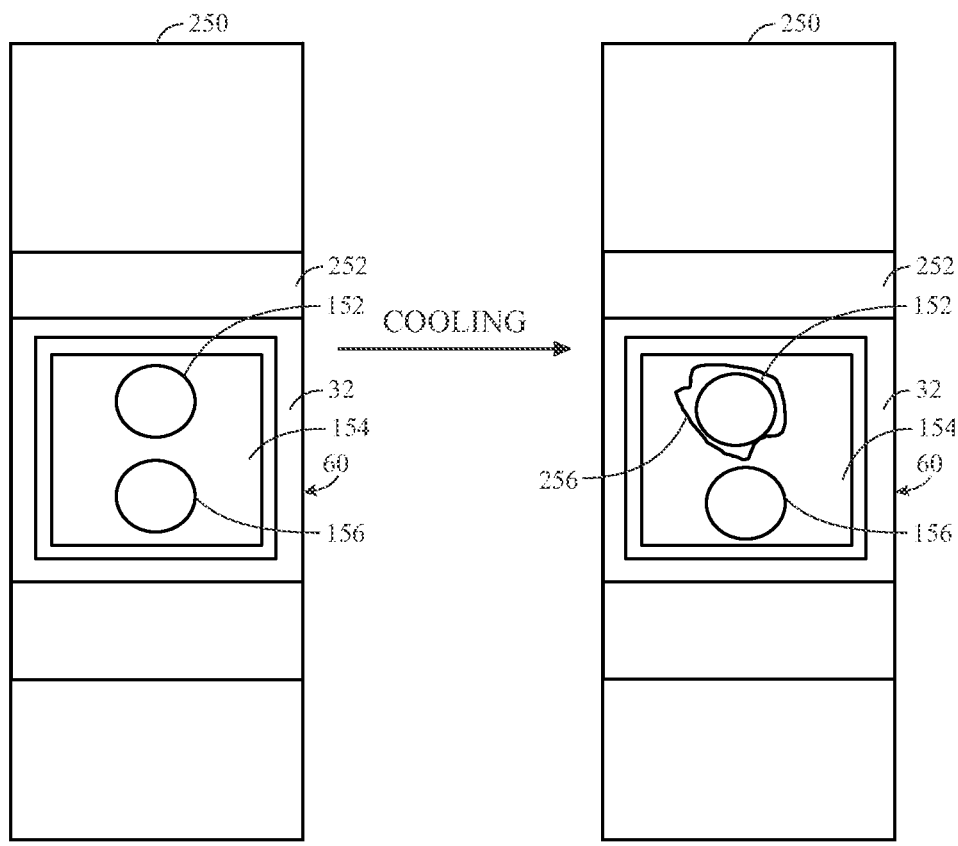
FIG. 13 illustrates a response of a second temperature sensitive component upon exposure to a temperature below a minimum value of the predetermined temperature range, in accordance with aspects of the present disclosure.

FIGS. 11-13 illustrate an embodiment of the packaging of the sensor assembly 150 as well as melting of the first component 152 and the second component 156 when the temperature of the fluid 62 goes outside of the predetermined temperature range.

FIG. 11 illustrates an embodiment of the sensor assembly 150 that includes a vessel 250 over which the first component 152, the second component 156, and the third component 60 are disposed. For example, the third component 60 (e.g., the sensor tag 32 and/or the pick-up coil 40) may be disposed directly over the vessel 250, such that the third component 60 contacts the vessel 250. Additionally, the second component 156 (e.g., component including a mixture of wax and PANI) may be disposed over the third component 60. Therefore, when the temperature of the fluid 62 reaches a value above the maximum value (e.g., 42° Celsius) of the predetermined temperature range, the second component 156 may be configured to melt and thereby releasing an embedded conductive material (e.g., PANI) and inhibit the response of the third component 60 (e.g., permanently disrupt the circuitry in the sensor tag 32). In certain embodiments, the filter 154 may be disposed over the second component 156. In other embodiments, the filter 154 may be positioned between the second component 156 and the third component 60.

In certain embodiments, the filter 154 is positioned between the first component 152 and the second component 156. Therefore, when the temperature of the fluid 62 reaches a value below the minimum value (e.g., 0° Celsius) of the predetermined temperature range, the first component may be configured to melt and eventually inhibit the response of the third component 60. For example, a portion of the melted first component 152 may be absorbed by the filter 154 to concentrate the melted first component 152 in an area approximately aligned with the third component 60. Therefore, the melted first component 152 may contact the third component 60 and disrupt the circuitry of the sensor tag 32. It should be noted that while the illustrated embodiment of FIG. 11 shows the filter 154 positioned between the first component 152 and the third component 60, the first component 152 may be positioned adjacent to the third component (e.g., the filter 154 is positioned above the first component 152).

Additionally, in certain embodiments, the first component 152, the filter 154, the second component 156, and/or the third component 60 may be secured to the vessel 250 by a protection package 252. The protection package 252 may include a physical barrier and/or a chemical barrier to block moisture from contacting the sensor assembly 150 (e.g., the first component 152, the filter 154, the second component 156, and/or the third component 60). Additionally, the protection package 252 may prevent liquids included in the sensor assembly 150 from evaporating and escaping from the sensor assembly 150. Furthermore, the protection package 252 may include an adhesive, such that the protection package 252 may adhere to the vessel 250 and secure the first component 152, the filter 154, the second component 156, and/or the third component 60 to the vessel 250. Accordingly, the first component 152, the filter 154, the second component 156, and/or the third component 60 may remain substantially stationary with respect to the vessel 250. It should be noted that in other embodiments, the first component 152, the filter 154, the second component 156, and/or the third component 60 may be secured to the vessel 250 using any suitable adhesive or other device configured to couple components of the sensor assembly 150 to one another.

The vessel 250, the first component 152, the filter 154, the second component 156, the third component 60, and/or the tape 252 may be disposed in a housing such that the gap 72 forms between the tape 252 and an inner wall of the housing. In certain embodiments, the pick-up coil 40 may be disposed on an outer wall of the housing. In other embodiments, the pick-up coil 40 may be disposed on the inner wall of the housing. In still further embodiments, the pick-up coil 40 may be disposed over the first and second components 152, 156 and be secured to the vessel 250 by the tape 252.

FIG. 12 illustrates a response (e.g., an irreversible response) of the second component 156 upon exposure to a temperature above the maximum value (e.g., 42° Celsius) of the predetermined temperature range, in accordance with aspects of the present disclosure. For example, in certain embodiments, the second component 156 may include the second chemical compound (e.g., a mixture of wax and PANI). The second chemical compound may be configured to melt upon exposure to a temperature above the maximum value (e.g., 42° Celsius) of the predetermined temperature range. As the temperature exceeds the maximum value of the predetermined temperature range, the second component 156 may transform from a solid state (e.g., a solid) to a liquid state. As the second component 156 melts and transitions to the liquid state, the embedded conductive materials (e.g., PANI) in the resulting liquidized second component 254 may contact the third component 60 and affect a response of the third component 60 (e.g., permanently disrupt circuitry of the sensor tag 32). In certain embodiments, the liquidized second component 254 may decrease the sensor tag 32 response (e.g., impedance) as a result of the liquid 254 causing a short in the circuitry of the sensor tag 32. Accordingly, the sensor tag 32 may no longer be used to monitor a volume of the fluid 62 in the vessel 250 and a user may be alerted that the fluid may have lost its efficacy.

Similarly, FIG. 13 illustrates a response (e.g., an irreversible response) of the first component 152 upon exposure to a temperature below the minimum value (e.g., 0° Celsius) of the predetermined temperature range, in accordance with aspects of the present disclosure. For example, in certain embodiments, the first component 152 may include the first chemical compound (e.g., conductive poloxamer). The first chemical compound may be configured to melt upon exposure to a temperature below the minimum value (e.g., 0° Celsius) of the predetermined temperature range. As the temperature decreases below the minimum value of the predetermined temperature range, the first component 152 may transform from a solid state (e.g., a gel) to a liquid state. As the first component 152 melts and transitions to the liquid state, the resulting conductive liquidized first component 256 may contact the third component 60 and affect a response of the third component 60 (e.g., permanently disrupt circuitry of the sensor tag 32). In certain embodiments, the liquidized first component 256 may decrease the sensor tag 32 response (e.g., impedance) as a result of the liquid 256 causing a short in the circuitry of the sensor tag 32. According, the sensor tag 32 may no longer be used to monitor a volume of the fluid 62 in the vessel 250 and the user may be alerted that the fluid may have lost its efficacy.

As shown in FIGS. 11-13, the filter 154 may be disposed between the first component 152 and the third component 60 such that the liquidized first component 256 may be concentrated over the third component 60 and the amount of liquidized first component 256 that contacts the third component 60 is maximized. Additionally, in certain embodiments, the filter 154 may serve to increase the time that it takes to short the circuitry of the third component 60 (e.g., the sensor tag 32). For example, it may not be desirable to decrease the sensor tag 32 response immediately upon reaching the minimum temperature (e.g., 0° Celsius) of the predetermined temperature range because there may be a lag period between the time that the first component 152 reaches the minimum temperature and the time at which the fluid 62 (e.g., liquid medicine, vaccine, and/or saline) reaches the minimum temperature. Therefore, using the filter as a barrier configured to increase the time it takes for the liquidized first component 256 (or liquidized second component 254) to contact the third component 60 and cause a short circuit may be desirable.

Figure 14:
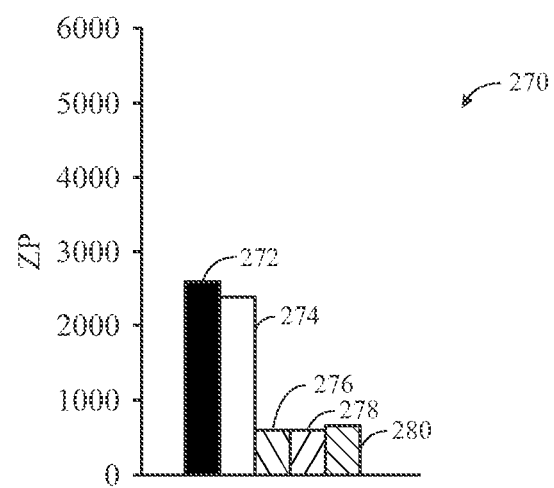
FIG. 14 is a graphical representation showing a response or memory function of the sensor assembly, in accordance with aspects of the present disclosure.

FIG. 14 is a graphical representation 270 showing a memory function of the sensor assembly 150. In certain embodiments, as the temperature of the fluid 62 reaches a value outside (e.g., above the maximum value or below the minimum value) of the predetermined temperature range, the response of the sensor tag 32 (e.g., impedance) is affected (e.g., permanently disabled). For example, graph 270 illustrates a first bar 272, a second bar 274, a third bar 276, a fourth bar 278, and a fifth bar 280, each having an impedance value that corresponds to the response of the sensor tag 32 (e.g., the larger the impedance value, the more responsive the sensor tag 32) after exposure to various environments for varying time frames. The first bar 272 represents the sensor assembly 150 at a temperature within the predetermined temperature range. The second bar 274 represents the sensor assembly 150 when exposed to a temperature near, but not below, the minimum value of the predetermined temperature range. As shown in the illustrated embodiment, the effect on the sensor assembly 150 is relatively small upon such temperature change. The third bar 276 represents the sensor assembly 150 after exposure to a temperature below the minimum value of the predetermined temperature range. As shown, the impedance value of the third bar 276 is significantly lower than that of the first and second bars 272, 274. In fact, the third bar 276 shows an approximately 75% change in impedance from the second bar 274.

Moreover, the fourth bar 278 represents the sensor assembly 150 one day after exposure to the temperature below the minimum value of the predetermined temperature range. As shown, the response of the sensor tag 32 remains affected one day after exposure. In other words, the sensor tag 32 does not recover once the temperature of the fluid 62 returns to a value within the predetermined temperature range. Therefore, the sensor tag 32 can be said to have a memory function, in that once the fluid 62 reaches a temperature outside of the predetermined temperature range, the sensor tag 32 response is permanently affected. The fifth bar 280 represents the sensor assembly 150 eight days after exposure to the temperature below the minimum value of the predetermined temperature range. As shown, the impedance of the fifth bar 280 increases slightly. However, the response of the sensor tag 32 is still significantly lower than that exhibited when the temperature of the fluid 62 was within the predetermined temperature range. Therefore, the response of the sensor tag 32 does not return to the pre-exposure level after a significant time period (e.g., 8 days)

It should be recognized that although graph 270 illustrates a sensor tag 32 having a memory function (e.g., a permanent change in sensor tag 32 response), other embodiments of the present disclosure may include a sensor tag 32 that recovers after exposure to a temperature outside of the predetermined temperature range. For example, the sensor tag 32 response may decrease significantly upon exposure to a temperature outside of the predetermined temperature range, but subsequently recover upon the temperature returning to a value within the predetermined temperature range. In any event, exposure to a temperature outside of the predetermined temperature range may cause the sensor tag 32 response to decrease, thereby tuning and/or inhibiting the ability of the sensor assembly 150 to monitor a volume of the fluid 62 in the vessel 250.

Figure 15A:
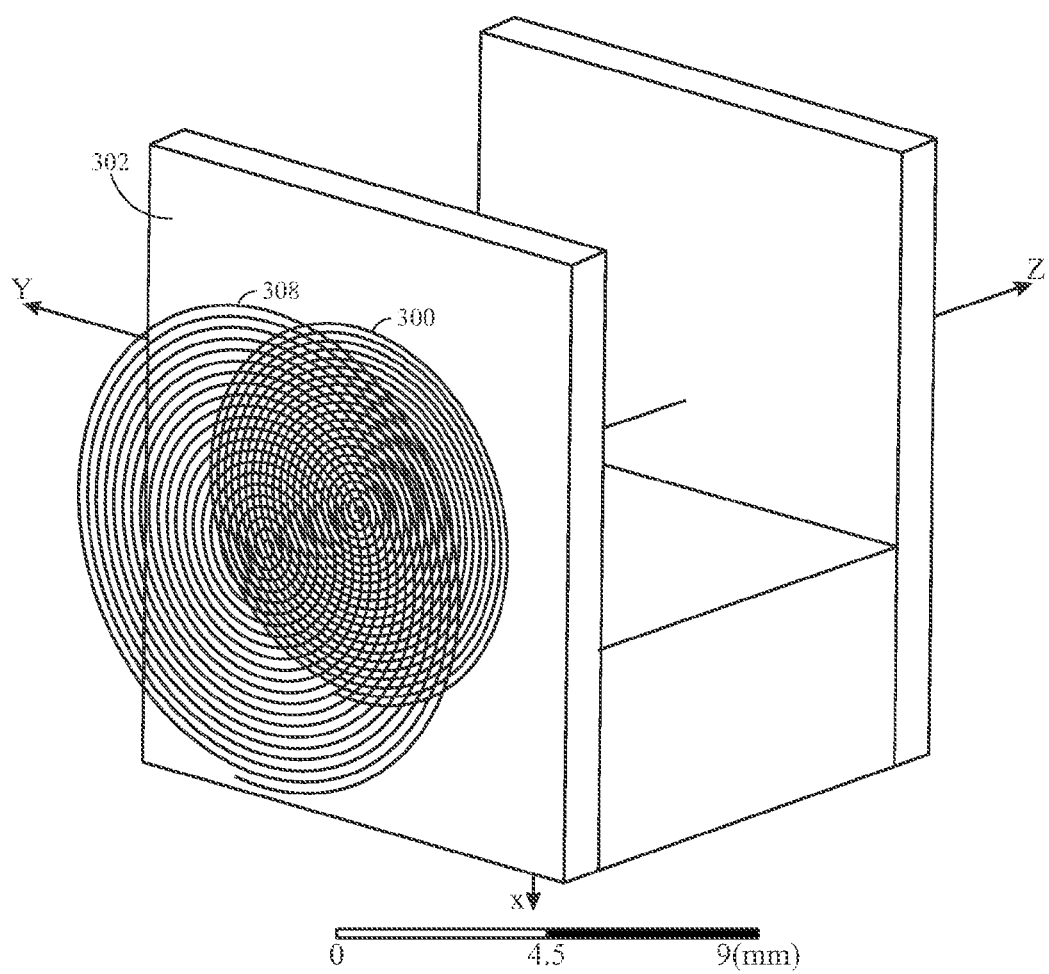
FIG. 15A illustrates a perspective view of a first sensor tag disposed on a flat surface and a flat pick-up coil.
Figure 15B:
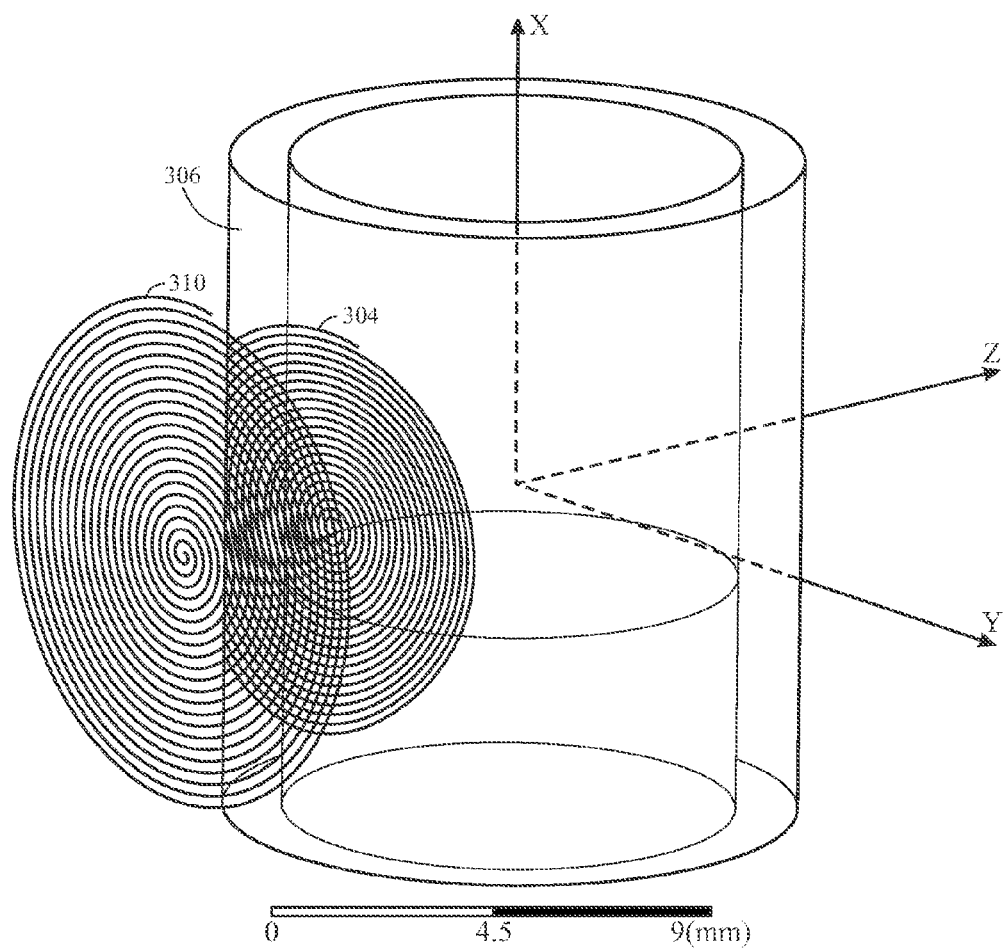
FIG. 15B illustrates a perspective view of a second sensor tag disposed on a curved surface and a flat pick-up coil, in accordance with aspects of the present disclosure.

Another feature of the sensor assembly 150 that may affect the sensor tag 32 response may be the shape of the vessel 250. For example, FIG. 15A illustrates a perspective view of a first sensor tag 300 disposed on a flat surface 302 and FIG. 15B illustrates a perspective view of a second sensor tag 304 disposed on a curved surface 306. Additionally, FIG. 15A shows a first pick-up coil 308 positioned a first distance from the first sensor tag 300 and FIG. 15B shows a second pick-up coil 310 positioned a second distance from the second sensor tag 304. In some instances, the curved surface 306 of the vessel 250 (e.g., a syringe) may affect the response of the second sensor tag 304. For example, as shown in the illustrated embodiments of FIGS. 15A and 15B, the first pick-up coil 308 is directly aligned with the first sensor tag 300 (e.g., all portions of the first sensor tag 300 are the same distance from the first pick-up coil 308) because the first sensor tag 300 is disposed over the flat surface 302. Conversely, the second pick-up coil 310 is not directly aligned with the second sensor tag 304 because the second sensor tag 304 is disposed on the curved surface 306. As shown in the illustrated embodiment, the second sensor tag 304 wraps around the curved surface 306, such that portions of the second sensor tag 304 are positioned further from the second pick-up coil 310 than other portions, which may affect the response of the second sensor tag 304.

Figure 16:
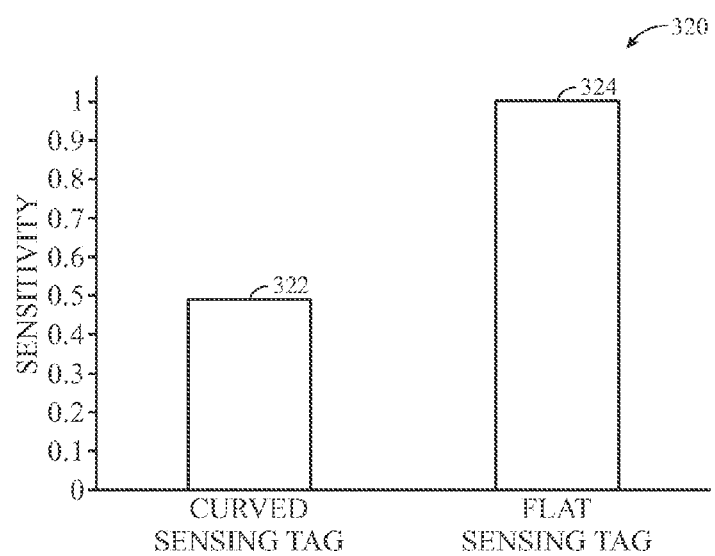
FIG. 16 illustrates a graphical representation of an effect of a curved surface on a response of the sensor assembly, in accordance with aspects of the present disclosure.

FIG. 16 illustrates a graphical representation 320 of the effect of the curved surface 306 on the response of the second sensor tag 304. The graph 320 includes a first bar 322 and a second bar 324. The first bar 322 represents a sensitivity of the second sensor tag 304 disposed on the curved surface 306 and having the flat, second pick-up coil 310, whereas the second bar 324 represents a sensitivity of the first sensor tag 300 disposed on the flat surface 302 and having the first pick-up coil 308. As shown in the illustrated embodiment, the sensitivity of the second sensor tag 304 and the second pick-up coil 310 is approximately half the sensitivity of the first sensor tag 300 and the first pick-up coil 308. Therefore, because portions of the second sensor tag 304 are positioned further from the second pick-up coil 310 than other portions, the sensitivity of the second sensor tag 304 and second pick-up coil 310 is significantly less than the first sensor tag 300 and the first pick-up coil 310. Therefore, it is now recognized that using a curve shaped pick-up coil may increase the sensitivity of a sensor tag disposed on the curved surface 306.

Figure 17:
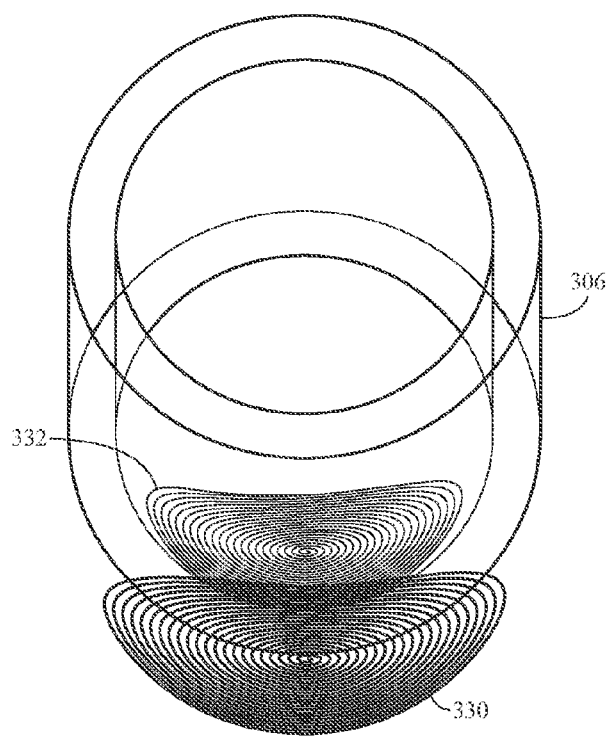
FIG. 17 illustrates an embodiment of a curved pick-up coil that may increase a sensitivity of a sensor tag disposed on a curved surface, in accordance with aspects of the present disclosure.

FIG. 17 illustrates an embodiment of a third pick-up coil 330 that may increase the sensitivity of a third sensor tag 332 disposed on the curved surface 306. For instance, the third pick-up coil 330 may include a curved shape that conforms to the curved surface 306. Therefore, when the third sensor tag 332 wraps around the curved surface 306, the distance between the third pick-up coil 330 and the third sensor tag 332 remains approximately equal across all portions of the third sensor tag 332.

Figure 18:
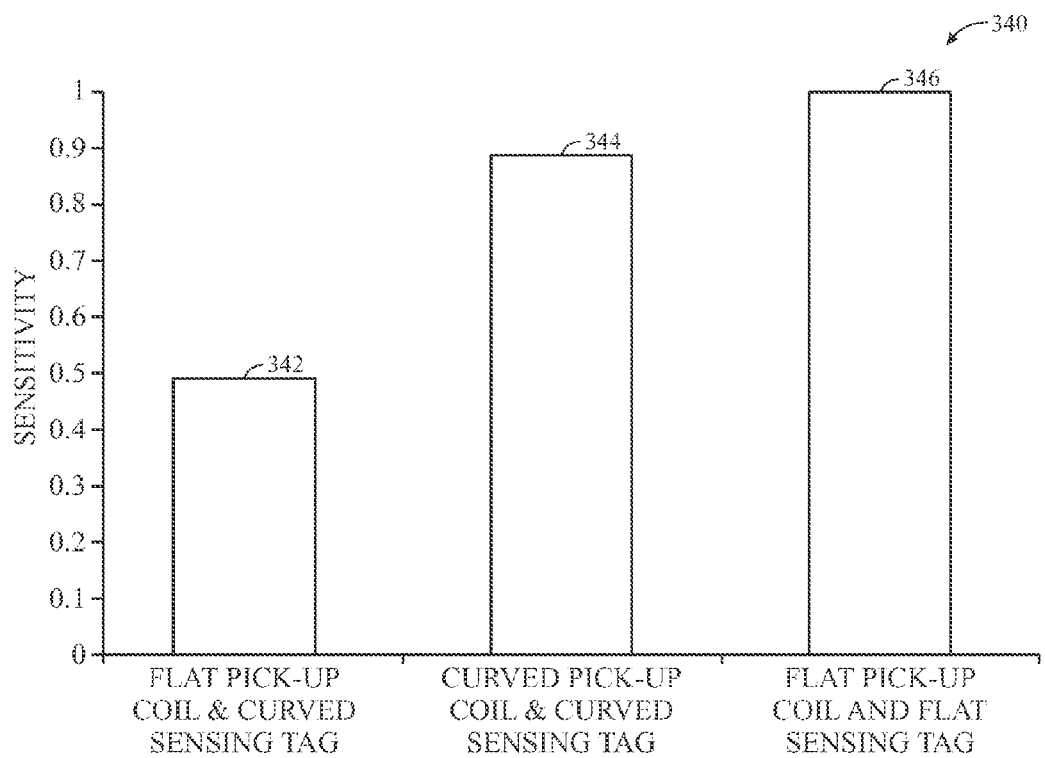
FIG. 18 illustrates a graphical representation of a sensitivity of three different combinations of curved and flat pick-up coils and sensor tags, in accordance with aspects of the present disclosure.

FIG. 18 illustrates a graphical representation 340 of the sensitivity of the third pick-up coil 330 and the third sensor tag 332 in comparison to the first sensor tag 300 and the first pick-up coil 308 as well as to the second sensor tag 304 and the second pick-up coil 310. For example, the graph 340 includes a first bar 342 representing the sensitivity of the second sensor tag 304 and the second pick-up coil 310 (e.g., a sensor tag on a curved surface with a flat pick-up coil); a second bar 344 representing the sensitivity of the third sensor tag 332 and the third pick-up coil 330 (e.g., a sensor tag on a curved surface with a curved pick-up coil); and a third bar 346 representing the sensitivity of the first sensor tag 300 and the first pick-up coil 308 (e.g., a sensor tag on a flat surface with a flat pick-up coil). As shown, the third sensor tag 332 and the curved, third pick-up coil 330 have a greater sensitivity than the second sensor tag 304 and the flat, second pick-up coil 310. Additionally, the third sensor tag 332 and the curved, third pick-up coil 330 has a sensitivity approximately 10% less than the first sensor tag 300 and the first pick-up coil 308. Therefore, the sensitivity of a sensor tag disposed on the curved surface 306 may be significantly improved by utilizing a curve-shaped pick-up coil.

Technical effects of the present disclosure include a sensor assembly configured to monitor and measure an amount of volume of a fluid (e.g., liquid medicine, vaccine, and/or saline) in a vessel using a sensor tag and a pick-up coil. Additionally, the present disclosure seeks to monitor the temperature of the fluid (e.g., liquid medicine, vaccine, and/or saline) and determine when the temperature reaches a value outside of a predetermined temperature range. In certain embodiments, when the temperature reaches a value outside of the predetermined temperature range, an indicative warning or caution may be produced. Additionally, the ability of the sensor assembly to monitor and measure the amount of volume of the fluid in the vessel (or dispensed from the vessel) may be inhibited when the temperature reaches a value outside of the predetermined temperature range. The effect on the response of the sensor tag may be permanent (e.g., a memory function) or temporary (e.g., the sensor tag response recovers when the temperature returns to a value within the predetermined temperature range). Certain aspects of the present disclosure seek to create an enhanced medication dispension device that accurately monitors a dispension rate of medication, while also having the ability to produce an alert or caution when dispension may be undesirable.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A sensor assembly, comprising:
a first component configured to transition from a substantially solid state to a substantially liquid state when a temperature of the sensor assembly decreases to a first value below a minimum value of a predetermined temperature range;
a second component configured to transition from a substantially solid state to a substantially liquid state when the temperature of the sensor assembly increases to a second value above a maximum value of the predetermined temperature range; and
a third component configured to monitor a volume of fluid disposed in a vessel when the temperature of the sensor assembly is within the predetermined temperature range.

2. The sensor assembly of claim 1, wherein the fluid comprises a liquid medicine, a vaccine, or a saline solution.

3. The sensor assembly of claim 1, wherein the first component comprises a first chemical compound.

4. The sensor assembly of claim 3, wherein the first chemical compound comprises a poloxamer or a poly(n-isopropylacrylamide).

5. The sensor assembly of claim 3, wherein the second component comprises a second chemical compound, different from the first chemical compound.

6. The sensor assembly of claim 5, wherein the second chemical compound comprises a mixture of wax and a conducting material, and wherein the conducting material is polyaniline (PANT), doped PANI derivatives, polypyyroles, graphitized carbon, copper, a conducting polymer, or any combination thereof.

7. The sensor assembly of claim 1, wherein the third component comprises a sensor tag and a pick-up coil, and wherein the pick-up coil is configured to emit an electromagnetic field to detect a signal produced by the sensor tag.

8. The sensor assembly of claim 7, wherein the sensor assembly comprises a radio frequency-based (RF) transducer.

9. The sensor assembly of claim 7, wherein a frequency of the third component is configured to increase as the volume of the fluid in the vessel decreases.

10. The sensor assembly of claim 7, wherein the sensor tag is configured to record an incident when the temperature of the sensor assembly reaches a value outside of the predetermined temperature range and to block the third component from monitoring the volume of the fluid in the vessel when the temperature of the sensor assembly reaches the value outside of the predetermined temperature range.

11. The sensor assembly of claim 7, wherein one or both of a melted first component and a melted second component are configured to cause a short in the sensor tag and inhibit monitoring the volume of the fluid in the vessel when the temperature of the fluid reaches the first value or the second value.

12. The sensor assembly of claim 11, wherein an impedance value of the sensor tag decreases when the melted first component or the melted second component contacts the sensor tag.

13. The sensor assembly of claim 1, wherein the predetermined temperature range comprises a maximum value and a minimum value.

14. The sensor assembly of claim 1, wherein the vessel is a syringe.

15. A method, comprising:
monitoring a volume of fluid in a vessel;
determining whether a temperature of the fluid in the vessel is outside of a predetermined temperature range using a first component and a second component, the first component is configured to transition from a substantially solid state to a substantially liquid state when the temperature of the fluid decreases to a value below a minimum value of the predetermined temperature range, and the second component is configured to transition from a substantially solid state to a substantially liquid state when the temperature of the fluid increases to a value above a maximum value of the predetermined temperature range;
producing an indicator warning against dispension of the fluid from the vessel when the temperature is outside of the predetermined temperature range; and
blocking the monitoring of the volume of the fluid in the vessel when the temperature reaches a value outside of the predetermined temperature range.

16. The method of claim 15, comprising inhibiting monitoring of the volume of the fluid in the vessel when the temperature of the fluid is outside of the predetermined temperature range.

17. The method of claim 15, wherein producing the indicator warning against dispension comprises notifications on mobile devices or a visual cue on the vessel.

18. The method claim 15, comprising recording an incident when the temperature of the sensor assembly reaches a value outside of the predetermined temperature range, and wherein the incident is configured to send a signal to permanently block monitoring the volume of the fluid in the vessel.

19. The method of claim 15, comprising determining whether the temperature of the fluid in the vessel has ever been outside of the predetermined temperature range and permanently blocking the monitoring of the volume of the fluid in the vessel when a determination is made that the temperature has ever been outside of the predetermined temperature range.

20. A sensor assembly, comprising:
a syringe configured to dispense a liquid medication;
a first component disposed on the syringe, wherein the first component comprises a first chemical compound configured to melt when a temperature of the liquid medication reaches a first value below a minimum value of a predetermined temperature range;
a second component disposed on the syringe, wherein the second component comprises a second chemical compound configured to melt when the temperature of the liquid medication reaches a second value above a maximum value of the predetermined temperature range;
a filter disposed between the first component and the second component;
a third component disposed on the syringe, wherein the third component comprises a sensor tag, the third component is configured to monitor a volume of the liquid medication in the vessel when the temperature of the fluid is within the predetermined temperature range, and a response of the sensor tag decreases when one or both of the first component and the second component melts; and
a protection package comprising a barrier configured to block moisture from contacting the sensor tag.

21. The sensor assembly of claim 20, wherein the filter comprises a microfiber filter.

22. The sensor assembly of claim 21, wherein the microfiber filter is configured to absorb, form a barrier to, or concentrate one or both of a melted first component and a melted second component over the sensor tag such that one or both of the melted first component and the melted second component contact the sensor tag and decrease the response of the sensor tag.

23. The sensor assembly of claim 22, wherein the response of the sensor tag is permanently changed upon contact with one or both of the melted first component and the melted second component.

24. The sensor assembly of claim 20, wherein protection package comprises an adhesive, and wherein the first component, the second component, the filter, and the third component are disposed on the syringe via the protection package.

25. The sensor assembly of claim 20, wherein the pick-up coil comprises a curved shape.

26. The sensor assembly of claim 20, wherein the third component is configured to detect and record an incident when the temperature of the sensor assembly reaches a value outside of the predetermined temperature range, and wherein the third component is configured to permanently block monitoring the volume of the fluid in the vessel when the incident is recorded.

* * * * *